United States Patent
Kidd

[11] Patent Number: 5,958,778
[45] Date of Patent: Sep. 28, 1999

[54] CONTAINER FOR DRYING BIOLOGICAL SAMPLES, METHOD OF MAKING SUCH CONTAINER, AND METHOD OF USING SAME

[75] Inventor: Geoffrey Kidd, Germantown, Md.

[73] Assignee: The United States of America as represented by the Department of Health and Human Services, Washington, D.C.

[21] Appl. No.: 08/717,114

[22] Filed: Sep. 20, 1996

Related U.S. Application Data

[60] Provisional application No. 60/004,195, Sep. 22, 1995.

[51] Int. Cl.$^6$ .................................................. B04B 15/00
[52] U.S. Cl. ............................ 436/45; 436/178; 422/72; 422/101
[58] Field of Search ................................ 422/58, 72, 100, 422/101, 102, 104; 436/178, 180, 45; 215/230, 307, 308, 330

[56] References Cited

U.S. PATENT DOCUMENTS

| | | | |
|---|---|---|---|
| 3,215,500 | 11/1965 | Bittner | 422/101 |
| 3,300,051 | 1/1967 | Mitchell et al. | 210/339 |

(List continued on next page.)

FOREIGN PATENT DOCUMENTS

| | | | |
|---|---|---|---|
| 0 337 677 A3 | 10/1989 | European Pat. Off. | B65D 51/16 |
| 0 341 372 | 11/1989 | European Pat. Off. | |
| 0 343 596 A3 | 2/1990 | European Pat. Off. | F26B 5/06 |
| 0 343 596 B1 | 3/1992 | European Pat. Off. | F26B 5/06 |
| 74 30745 | 9/1976 | France | F26B 5/06 |
| 3628930 A1 | 5/1988 | Germany | B65D 51/16 |
| 63-98380 | 10/1986 | Japan | C12N 5/00 |
| 394 945 | 12/1965 | Switzerland | |
| 995930 | 6/1969 | United Kingdom | |
| WO 95/27180 | 10/1995 | WIPO | |
| WO 96/30274 | 10/1996 | WIPO | B65D 51/16 |

OTHER PUBLICATIONS

Lau et al., "An Improved Method of Microdialysis", Analytical Biochemistry 110, pp. 144–145, 1981.
Roder, Helga, Dr., Kunststoffe in der Verpackung, Kunststoff–Verpackungsfolien, Kunststoffe 71:5 (1981).
Brand et al., "Improved Microdialysis Techniques", Analytical Biochemistry 94, pp. 109–111 (1979).
Marusyk et al., "A Simple Method for Dialysis of Small–Volume Samples", Analytical Biochemistry 105, pp. 403–404 (1980).
Lau et al., "An Improved Method of Microdialysis", Analytical Biochemistry 110, pp. 144–145 (1981).
"High–Recovery Microcon Microconcentrators", Amicon A Grace Company, pp. 1–8 (1993).
Amicon Price List, Amicon, Inc. 2 pp. (1994).
"Micropure Particle Separators", Amicon A Grace Company, pp. 1–6 (1994).
"Choosing the Correct Molecular Weight Cut–Off for Concentration and Desalting", Amicon A Grace Company, pp. 1–4 (1994).
"Flow Rates of Centriprep, Centricon, Microcon and Centrifree Centrifugal Devices", Amicon A Grace Company, pp. 1–2 (1994).
"The Fisher Catalog", Fisher Scientific, 5 pp. (1994).
"Passivation of Microcon Microconcentrators for Improved Recovery", Amicon A Grace Company, 2 pp. (Undated).
"Protein and Peptide Recovery from Polyacrylamide Gel with Micropure Inserts and Microcon Microconcentrators", Amicon A Grace Company, 2 pp. (Undated).

*Primary Examiner*—Jill Warden
*Attorney, Agent, or Firm*—Merchant & Gould P.C.

[57] ABSTRACT

A container suitable for high speed centrifugation is provided with a cap carrying a microbe-impermeable filter means. The filter means permits gas flow into and out of the container but prevents microbes from entering the container. A method of making such a container is also described. A preferred embodiment is for a container that can be used as a microcentrifuge tube. A method of drying, e.g., lyophilizing, a biological sample using the container is also provided.

25 Claims, 1 Drawing Sheet

5,958,778
Page 2

U.S. PATENT DOCUMENTS

| | | | |
|---|---|---|---|
| 3,326,401 | 6/1967 | Long | 215/308 |
| 3,391,466 | 7/1968 | Brouwer et al. | 34/289 |
| 3,512,940 | 5/1970 | Shapiro | 23/259 |
| 4,057,168 | 11/1977 | Bosshold | 220/209 |
| 4,241,188 | 12/1980 | Materia et al. | 435/296 |
| 4,271,973 | 6/1981 | Quagliaro et al. | 215/308 |
| 4,289,248 | 9/1981 | Lynn | 215/330 |
| 4,292,972 | 10/1981 | Pawelchak et al. | 128/296 |
| 4,456,137 | 6/1984 | Lyman | 215/230 |
| 4,674,640 | 6/1987 | Asa et al. | 215/230 |
| 4,707,452 | 11/1987 | Friswell | 436/177 |
| 4,755,356 | 7/1988 | Robbins et al. | 422/102 |
| 4,763,804 | 8/1988 | O'Connell | 215/307 |
| 4,872,872 | 10/1989 | Polak | 604/405 |
| 4,891,134 | 1/1990 | Vcelka | 210/359 |
| 4,915,847 | 4/1990 | Dillon et al. | 210/737 |
| 4,956,103 | 9/1990 | Jessop et al. | 210/787 |
| 4,962,044 | 10/1990 | Knesel, Jr. et al. | 436/177 |
| 4,990,253 | 2/1991 | Vcelka | 210/359 |
| 5,047,347 | 9/1991 | Cline | 435/296 |
| 5,079,170 | 1/1992 | Rosman et al. | 436/178 |
| 5,100,623 | 3/1992 | Friswell | 422/68.1 |
| 5,156,811 | 10/1992 | White | 422/100 |
| 5,160,413 | 11/1992 | Allison | 203/35 |
| 5,176,799 | 1/1993 | Roe et al. | 202/184.3 |
| 5,224,515 | 7/1993 | Foster et al. | 138/89 |
| 5,225,165 | 7/1993 | Perlman | 422/102 |
| 5,254,314 | 10/1993 | Yu et al. | 422/102 |
| 5,270,011 | 12/1993 | Altherr | 422/102 |
| 5,309,649 | 5/1994 | Bergmann et al. | 34/284 |
| 5,334,130 | 8/1994 | Glater et al. | 494/4 |
| 5,364,595 | 11/1994 | Smith | 422/100 |
| 5,376,273 | 12/1994 | Pacheco et al. | 210/490 |
| 5,380,435 | 1/1995 | Stokes et al. | 210/361 |
| 5,382,408 | 1/1995 | Perlman | 422/102 |
| 5,391,496 | 2/1995 | Kayal et al. | 435/286 |
| 5,398,837 | 3/1995 | Degrassi | 220/337 |
| 5,407,087 | 4/1995 | Giblin et al. | 215/260 |
| 5,522,155 | 6/1996 | Jones | 34/286 |
| 5,523,236 | 6/1996 | Nuzzo | 435/304.1 |
| 5,648,271 | 7/1997 | Kempe | 436/178 |
| 5,732,837 | 3/1998 | Jones | 215/311 |

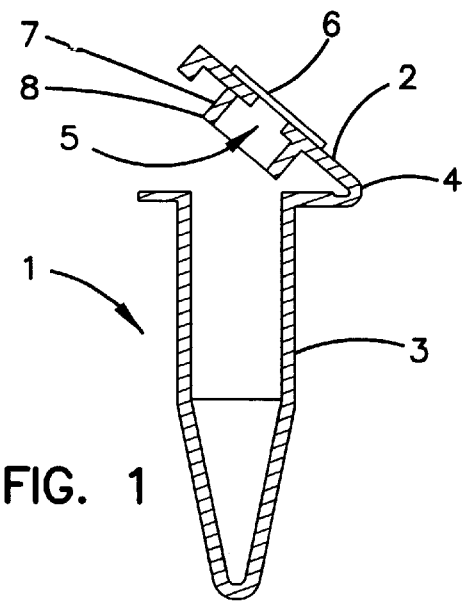
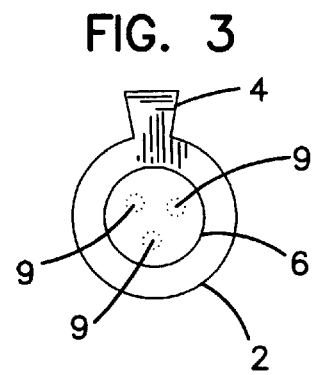
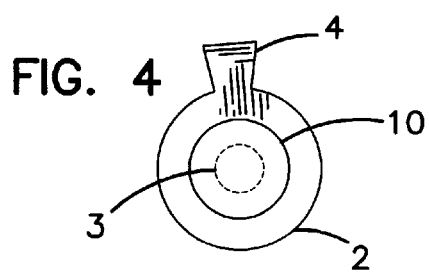
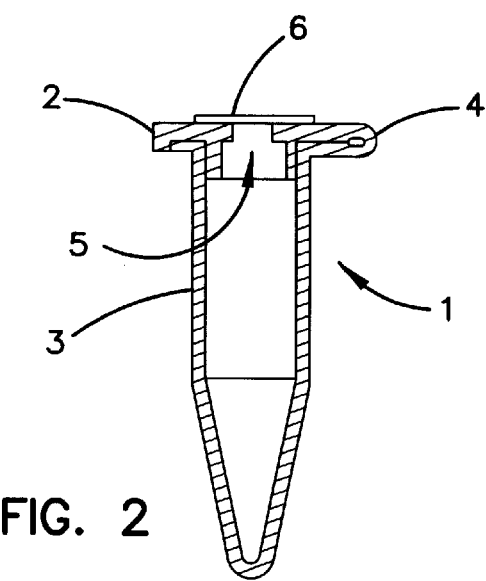
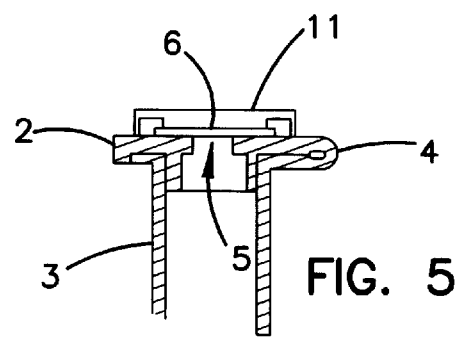
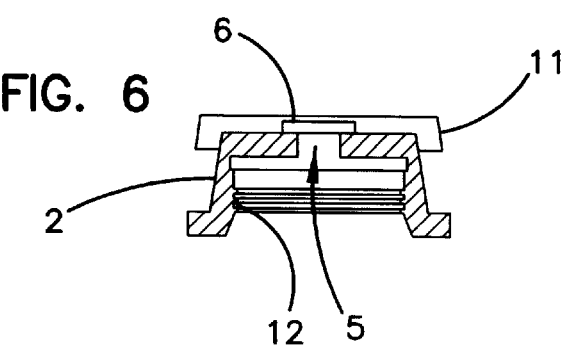

CONTAINER FOR DRYING BIOLOGICAL SAMPLES, METHOD OF MAKING SUCH CONTAINER, AND METHOD OF USING SAME

RELATED APPLICATION

This application claims the benefit of U.S. Provisional Application No. 60/004,195, filed Sep. 22, 1995.

TECHNICAL FIELD

The present invention relates to sterile containers for drying biological samples, and related methods. More particularly, the present invention relates to microcentrifuge tubes and methods of using the same.

BACKGROUND ART

It is often desired to dry biological samples in order to preserve their shelf life and activity. One drying technique is lyophilization, which is a commonly employed freeze-drying technique. Still other biological materials, such as long chain DNA molecules and cell components, are desired to be dried at a temperature above 0° C., i.e., above freezing, in order to prevent their destruction by the forces of freezing. Inasmuch as the present invention is not limited to lyophilization, drying above and below the freezing point are discussed interchangeably.

Usually, after a lyophilization process is completed the freeze-dried compound is stored in a freezer, e.g., at –70° C., although lyophilization can sometimes obviate the need for freezing all together. For example, according to the manufacturer's product profile sheet, Endothelial Cell Growth Supplement (ECGS) is stable for at least 18 months when stored at 4° C. in lyophilized form, but only one month when stored in a solubilized form at –20° C.

Lyophilization of compounds is particularly useful when growing cells in a culture medium where the lyophilized compounds include peptides or growth factors. These compounds are generally provided in minute quantities due to their expense and/or potency, and they are usually extremely perishable. Lyophilization is observed to extend their shelf life.

Typically, lyophilization is carried out in a centrifugal apparatus, such as a Speed-Vac® centrifuge. The Speed-Vac® is placed in a vacuum chamber. The sample is placed in a microcentrifuge tube which is a small plastic tube (0.5, 1, or 2 mLs) typically tapered, conical or rounded, and closed at one end. Because the vacuum used in lyophilizing is extremely high (e.g., 50–500 milli.Torr), some of the liquid in the microcentrifuge tube vaporizes immediately and forces out much of the remaining solution from the tube. By applying a centrifugal force, the liquid is pushed down to the bottom of the tube in an effort to prevent the liquid from jetting out when the liquid gassifies. After lyophilization is complete, the vacuum is turned off, thereby allowing the vacuum chamber and the interior volume of the tube to return to ambient pressure.

In order to use stored dried compounds, they must be dissolved (if not already stored in solution), then filtered-sterilized, which filters out all living cells, dust, and other unwanted materials. The volume of the solution at this stage is small, e.g., 1 ml. After filter-sterilization, the compounds are usually distributed in aliquots, e.g., of 50 μl each, and unused aliquots are stored in a freezer. This avoids the necessity of repeatedly freezing and thawing the compounds, which shortens their shelf life.

Another lyophilization method entails leaving the microcentrifuge tube lid open during lyophilization. After the vacuum is terminated, the lid is then closed. This method produces an unsterile sample, which must be resterilized by filter-sterilization. However, in this method, that portion of the stored sample adsorbed to the filter is lost.

Still another method is to perform lyophilization in a sterile environment such as a clean room. However, this requires incurring the additional expense of maintaining a clean room environment.

Yet another method proposes sterile gas exchange through a membrane in an enclosed sterile environment, see, for example, U.S. Pat. No. 5,398,837 and a cell culture flask manufactured by Costar (catalog number 3056). However, neither of these methods is suitable for lyophilization using a centrifuge since the cell culture flasks cannot be centrifuged at high speeds. Moreover, the cell culture flasks provide a slow gas exchange between the outside environment and the cell culture being grown. Furthermore, the porosity of the membrane is such that it is permeable to gas but not to microbes, e.g., having diameters above about $0.22\mu$.

Accordingly, a need exists for a container for a material that can be subjected to high centrifugal forces, as during a drying procedure, but which permits sterile gas exchange between the interior of the container and the external environment. Such a container need only be capable of permitting drying while preventing microbial contamination, independent of centrifugation, for those applications not requiring centrifugation.

SUMMARY OF THE INVENTION

The present invention is for a method of drying a solid, liquid, or gaseous sample containing a vaporizable material, such as when drying a solid material of a liquid solvent for the solid material. Such a method comprises providing a container containing the sample, which container defines an opening with the opening sealed substantially by a filter element (means), such as a membrane. The filter element permits permeation of the vaporizable material, e.g., gas, solid, liquid, or combination thereof, while substantially preventing permeation of microbes into the container. The drying method further entails permitting at least a portion of the vaporizable material to permeate the filter means, thereby affording at least a partial drying of the sample without substantial microbial contamination thereof.

The present invention also is for a method of venting a sample to its surroundings. As used herein, "venting" refers to permitting the contents of a container to come into contact with a gas external of the container either by permitting a gas flow into the container from outside or by permitting volatile components within the container to pass the external environment. Such venting method entails providing a container having an opening sealed substantially with a filter means, which permits permeation of at least one gas and substantially prevents permeation of microbes. Preferably, the container is configured to withstand a high speed centrifugation of 50 or more times the force of gravity, and permits the gas to enter or exit the container by permeating through the filter means. Such method thereby affords venting of the sample in the container without substantially contaminating the sample with microbes.

A container assembly aspect of the invention comprises a container having a closed end and an open end, which defines an interior volume therein, with the container capable of withstanding centrifugation at about 50 or more times the force of gravity. The container assembly also comprises a cap having an open position and a closed position for sealing the open end of the container, which cap carries a microbe-impermeable filter means that permits gas flow into the interior volume from external the container and permits gas flow out from the interior volume.

Relatedly, a container assembly is also contemplated which comprises a container having a closed end and an open end that defines an interior volume therein, where the container is shaped to conform to the shape of a centrifuge rotor or bucket. The container assembly also comprises a cap having an open position and a closed position for sealing the open end, with the cap including a microbe-impermeable filter means as described hereinabove.

In a preferred embodiment an instant container is provided as a microcentrifuge tube. In another embodiment, the container can be a centrifuge bottle, which conforms either to a bucket that hooks onto a centrifuge rotor or conforms to a well provided in the rotor of the centrifuge. Such a centrifuge bottle usually has a capacity of 100 mL or greater, and has a flat bottom supported by the well or bucket into which it is placed.

Also contemplated is a method of making a container assembly, and associated cap, of the invention which entails providing a cap which defines an aperture therein, covering the entire aperture with a filter means that does not permit substantial permeation of materials having a diameter of at least about 0.2 microns, and securing the filter means to the cap with an adhesive, a cement, a welding, or a mechanical fastening.

Still other objects and advantages of the present will become apparent to those skilled in the art from the following detailed description, wherein only preferred embodiments are shown and described. Accordingly, the drawings and description are to be regarded as only illustrative in nature, and not as limiting.

BRIEF DESCRIPTION OF THE DRAWINGS

FIG. 1 depicts a side cross-sectional view of a centrifuge tube according to a first embodiment of the present invention with the cap in the open position.

FIG. 2 is a cross-sectional view of the centrifuge tube of FIG. 1 with the cap in the closed position.

FIG. 3 is a top view of the centrifuge tube of FIG. 2 according to a first embodiment of the invention.

FIG. 4 is a top view of the centrifuge tube of FIG. 2 according to a second embodiment of the present invention.

FIG. 5 is a side cross-sectional view of a centrifuge tube which includes a cover according to a third embodiment of the present invention.

FIG. 6 is a side cross-sectional view of a cap according to a fourth embodiment of the present invention.

DETAILED DESCRIPTION OF THE PREFERRED EMBODIMENTS

The present invention is a method of drying, e.g., lyophilizing, a sample in a container, which sample contains a vaporizable material. A "vaporizable material" as used herein refers to a solid, liquid or gas, or combination thereof, such as an aerosol, which can enter the vapor phase. Preferably, such a vaporizable material is a solvent for one or more biological molecules, wherein it is desired to remove the solvent preferentially from the container.

Preferred samples for drying with an instant container include synthetic and natural peptides, DNA, RNA, oligonucleotides, such as PCR primers, proteins, and hybrid molecules. Also, cells and intracellular structures can be used. In some cases it will be necessary to heat the sample sufficiently to prevent it from freezing, as when the sample contains materials that would be damaged by freezing.

A container suitable for use with the present invention can be made of any material which does not react with the components placed therein and which withstands the centrifuge pressures placed upon it. Thus, a preferred tube is a disposable, polypropylene microcentrifuge tube having an attached lid, such as that known as epppendorf Safe-Lock (TM), available from Sigma Chemical Co (St. Louis, Mo.).

With respect to the filter means used to prevent microbe contamination of a sample placed in an instant container, it is preferably composed of a plastic, such as nylon, however, other materials may suffice. Whenever, nylon is used, it is preferred to glue the nylon filter to a cap with an epoxy resin that does not dissolve the nylon. A preferred epoxy resin is fast curing, such as is available from Duro Corporation.

A filter means employed in the present invention is preferably a membrane. For example, suitable membranes available from Millipore include the following:

Durapore (polyvinylidene fluoride), pore size $0.22\mu$

MF-Millipore (mixed cellulose esters), pore size $0.22\mu$ and smaller

Isopore Polycarbonate, pore size $0.2\mu$ and smaller Suitable membranes available from Pierce Chemical (Rockford, Ill.) include:

FilterPure (nylon 66), pore size $0.2\mu$

FilterPure (PTFE/polypropylene), pore size $0.2\mu$

Other suppliers and membrane materials can be readily identified by the skilled practitioner without undue experimentation.

The centrifuge tubes and bottles of the present invention include caps which have filter elements incorporated therein. The filter elements have pore sizes small enough, less than about $0.22\mu$, to prevent contaminants such as microbes, dust, and other unwanted materials from being drawn into the tubes or containers as the vacuum is released, while allowing air or other gases to enter the tubes or bottles during lyophilization.

The caps can be completely detachable from the centrifuge tubes or bottles, or the caps can be attached to the tubes and bottles by hingeable or similar connector structures. The caps can be of any conventional design in regard to the manner that they are connectable to the tubes or bottles. That is, the caps can be designed to be received in the open end of the tubes or bottles, or the caps can be designed so that the open end of the tubes or bottles are received in a lower recess of the cap. Alternatively, the caps can include annular recesses (edges) defined by concentric cylindrical structures so that the open end of the tubes or bottles are received in the annular recesses and the concentric cylindrical structures straddle the open end of the tubes or bottles. It is also within the scope of the present invention to utilize caps which can be attached to the tubes or bottles by internal or external threads which cooperate with complementary external or internal threads provided on the tube or bottles.

The tube and bottle caps of the present invention are provided with one or more openings in the top thereof. One or more filter elements are positioned to extend across the openings. The filter elements can be provided on an upper or lower surface of the cap as long as it extends across the opening(s). Alternatively, the filter element can be provided within the opening.

The opening may be of any desired shape; however, the use of circular openings may be more convenient from a manufacturing standpoint. It is noted that since the openings are provided for purposes of venting, they can be quite small. In prototype devices which were successfully tested, the openings were made by piercing the caps of microcentrifuge tubes with a needle. The resulting openings were approximately 0.2–0.5 mm in diameter. There is no upper limit on how large the openings may be; however, for larger openings it may be necessary to provide support structures across the openings to support the filter elements so that they are not pulled through the openings when the vacuum is released.

In order to protect the filter element (means) or keep the opening(s) from being plugged, a cover can be provided which can be secured to the top of the cap. Such a cover can be secured to the cap in the same manner as the cap itself is secured to the tube or bottle. Otherwise, the cover can be a relatively flat element that is secured to the cap by an adhesive. The cover may also be permanently attached to the cap and include a portion which can be torn-off and removed to expose the filter element. If the cover is permanently attached to the cap it should be vented.

With respect to drying a sample using an instant container, it may be preferable to position a desiccant outside the container so as to ensure complete drying of the sample or to prevent volatile materials from reentering the container. Suitable desiccants include activated alumina, calcium chloride, silica gel, zinc chloride, and the like.

As shown in FIG. 1, a cross-sectional view of a centrifuge tube according to a first embodiment of the present invention is depicted with the cap in the open position. The centrifuge tube 1 in FIG. 1 is of conventional design except for the cap structure. Alternatively, other conventional centrifuge tubes or bottles may be provided. The cap 2, which is attached to the tube body 3 by a hinge member 4, includes an opening 5 in the cap 2. The opening 5 is covered by a filter element 6. As discussed above, the filter element 6 can be provided on either the upper or lower surface of the cap 2 as long as it extends across the opening 5. Alternatively, the filter element 6 can be provided within opening 5.

The filter element 6 can be secured to the cap 2 by an adhesive or a cement. Alternatively, the filter element 6 can be secured to the cap 2 by a welding method such as heat welding, radio frequency welding or ultrasonic welding. It is also possible to secure the filter to cap 2, or in the opening 5 of the cap 2, by means of a mechanical element such as a retaining ring or recess, to which, or by which, the filter element 6 is attached to the cap. For example, a retaining ring having a diameter larger than the filter element 6 could be placed over the filter and secured to the cap 2. Similarly, a support ring or ledge could be provided in the bore of the opening 5 and the filter element 6 could be secured either directly to the support ring or the filter element could be secured to the support ring by a retaining ring.

The centrifuge tube 1 is constructed of a material(s) that does not adversely react with the compounds which are to come into contact therewith. Such centrifuge tubes and bottles are conventional in the art. Likewise, the filter element 6 and any supporting structures, including adhesives and cements should be selected so that they do not contaminate materials they come into contact with. A preferred material for the filter element 6 is nylon. The pore size of the filter element 6 can be selected as desired to prevent contaminants from entering the centrifuge tube 1. Microcentrifuge tubes were successfully tested where the filter element had a pore size of 0.2 microns. Extending downwardly from a lower surface of cap 2 is an annular sealing portion 7 having an outwardly extending semi-circular seal portion 8 at a distal end thereof.

FIG. 2 is a cross-sectional view of the centrifuge tube 1 of FIG. 1 with the cap 2 in the closed position. It is important that any filter means, or cap structure supporting the filter means seals the centrifuge tube 1 sufficiently so that contaminants, e.g. microbes, cannot be drawn into the tube except through the filter element 6 when the cap 2 is secured on the tube body 3. Accordingly, as referred to herein, such a container is said to be "substantially sealed" by the filter means. In this regard, as discussed above, the caps can be of any conventional design in regard to the manner that they are connectable to the tubes or bottles. As shown in FIG. 2, annular sealing portion 7 extends downwardly into tube 1. Seal portion provides a sterile seal along an inner surface of tube 1.

FIG. 3 is a top view of the centrifuge tube of FIG. 2 according to one embodiment of the present invention. In FIG. 3 the cap 2 is shown as including a plurality of spaced openings 9.

FIG. 4 is a top view of the centrifuge tube of FIG. 2 according to a second embodiment of the present invention. In FIG. 4 the cap 2 is shown as including a single opening 10 having a diameter larger than that of tube 1.

As discussed above, with respect to FIG. 3, the cap 2 can contain one or more openings 9 which can be of any desired shape. Since the opening(s) is/are provided for allowing gas exchange or escape as the liquid therein evaporates and for venting in air as the vacuum is released, it is sufficient to provide a single opening that is 0.2–0.5 mm in diameter. If larger openings are used, support structures can be provided across the openings to support the filter elements so that they are not pulled through the openings when the vacuum is released, or so that the filter elements are not sucked though the openings as the vacuum is applied.

FIG. 5 is a cross-sectional view of a centrifuge tube which includes a cover according to a third embodiment of the present invention. In order to protect the filter element 6 from accidental damage, a cover 11 can be provided. The cover 11 can be secured to the cap 2 in the same manner as the cap 2 itself is secured to the centrifuge tube body 3. Otherwise, the cover 11 can be a relatively flat element that is secured to the cap 2 by an adhesive. The cover 11 may also be permanently attached to the cap 2 and include a portion which can be torn-off and removed to expose the filter element 6 to allow air to vent through filter element 6 and through cap 2.

FIG. 6 is a cross-sectional view of a cap according to a fourth embodiment of the present invention. The cap 2 in FIG. 6 includes internal threads 12. This cap 2 can be secured to a centrifuge tube or bottle which includes cooperating external threads adjacent the open end thereof. Likewise, locking structures such as bayonet rings can be incorporated into the cap 2 and tube body 3.

The present invention is applicable to all types of vessels used for lyophilization, notably all types of capped test tubes, centrifuge tubes, vials, bottles, etc.

When using the centrifuge tubes of the present invention during a sterile lyophilization process, as the vacuum is terminated after lyophilization, air which is drawn into the centrifuge tube is filter-sterilized. That is, contaminants such as microbes, dust, and other unwanted materials are retained by the filter element so that they do not enter the centrifuge tube.

A device of the present invention can be used to dry materials used in microbial, tissue, organ, or plant culture, such as proteins, peptides, nucleic acids, etc., especially where a small volume is to be divided into smaller aliquots for storage. Such aliquots (e.g, 50 microliters) are difficult to filter-sterilize, so that filter-sterilization is best done prior to aliquoting and lyophilization.

In a typical sterile lyophilization procedure, according to the present invention, a compound of interest, e.g. a protein, peptide, nucleic acid, etc., in solution is placed in a container of the invention. The centrifuge tube is sealed with a cap having a filter element incorporated therein as described above, and placed in a centrifugal apparatus such as the Speed-Vac®.

A vacuum of approximately 50 to 500 milli.Torr is applied to the compound as the compound is centrifuged. The high vacuum causes some of the liquid in the solution to gassify and leave the solution. This phase change removes heat from the solution and tends to cause freezing simultaneously with drying of the material. As discussed above, the centrifugal force of the centrifuge tends to keep the liquid phase at the bottom of the centrifuge tube so that it does not jet out with the gassified portion of the solution.

After lyophilization is complete, the vacuum is turned off and ambient gas, such as air or an inert gas, is drawn into the centrifuge tube through the filter element in the cap. Passage of the ambient gas through the filter element causes filter-sterilization of the ambient gas and thus prevents contamination of the lyophilized compound.

As is apparent from the above discussion, a key advantage of the present invention is that it permits one to perform many operations sequentially in the same container. In particular, some or all of the following steps can be performed in a single tube or bottle:

(1) A sample can be aliquotted into the container;

(2) The container can be sealed, with gases passing through the filter means and possibly passing around the cap between its interface with the container body (as long as microbes cannot pass between the cap and container body);

(3) The sample can be dried, with or without lyophilizing;

(4) The sample can be vented to the external environment;

(5) The sample can be lyophilized, including applying a vacuum and centrifuging;

(6) The sample can be stored in the same container, e.g., in a freezer;

(7) A dried sample can be dissolved or reconstituted in the container, using water or other solvents;

(8) The sample can be agitated in the container to mix the components therein, which procedure usually deposits material on the inner walls of the container;

(9) The sample can be centrifuged in order to force components on the walls back down to the bottom of the container;

(10) Should particulate material form, e.g., when a protein becomes denatured, the centrifuging step gathers the particulates together which assists in future handling, e.g., by not clogging a pipette;

(11) The sample can be removed from the container for subsequent use; and

(12) If sample is left over, it can be relyophilized and the previous steps can be repeated.

Although the present invention has been described with reference to particular examples, one skilled in the art will appreciate that certain changes and modifications of the invention as set forth in the appended claims can be practiced without departing from the spirit and scope of the invention.

What is claimed is:

1. A method of drying a solid or liquid sample including a vaporizable material in a container, comprising the steps of:

providing said container containing said sample, said container defining an opening, which opening is sealed substantially with a filter means, which filter means permits permeation of said vaporizable material therethrough and substantially prevents permeation of microbes therethrough; and permitting at least a portion of said vaporizable material to permeate said filter means, including subjecting said sample to centrifugation, thereby affording at least a partial drying of said sample without substantial microbial contamination thereof.

2. A method of drying a solid or liquid sample including a vaporizable material in a container, comprising the steps of:

providing said container containing said sample, said container defining an opening, which opening is sealed substantially with a filter means, which filter means permits permeation of said vaporizable material therethrough and substantially prevents permeation of microbes therethrough, wherein said container has a shape that corresponds to a shape of a cavity in a centrifuge rotor or a shape of a cavity in a centrifuge bucket; and permitting at least a portion of said vaporizable material to permeate said filter means, including subjecting said sample to centrifugation, thereby affording at least a partial drying of said sample without substantial microbial contamination thereof.

3. A method of venting a sample contained in a container, comprising the steps of:

providing said container containing said sample, said container having an opening sealed substantially with a filter means, said filter means permitting permeation therethrough of at least one gas and substantially preventing permeation therethrough of microbes, said container being configured to withstand a high speed centrifugation of 50 or more times the force of gravity; and permitting said gas to enter or exit said container by permeating through said filter means, including subjecting said sample to centrifugation, thereby affording venting of said sample without substantially contaminating said sample with microbes.

4. The method of claim 1 or 3, wherein said providing step includes placing said sample in said container through said opening.

5. The method of claim 4, further comprising subsequently substantially sealing said opening at least in part with said filter means.

6. The method of claim 5, wherein said container includes a cap hingeably attached to a tube body, with said filter means carried by said cap, and wherein said substantially sealing step includes joining said cap with said tube body so as to substantially prevent microbes from passing between said cap and said tube body.

7. The method of claim 1 or 2, wherein said step of providing said sample in said container comprises the steps of:

inserting a sample injection means at least partially into said container through said opening; and providing at least a portion of said sample through said sample injection means into said container.

8. The method of claim 7, further including the steps of:

inserting said sample injection means through said filter means;

providing at least a portion of said sample through said sample injection means into said container while said sample injection means is inserted through said filter means; and subsequently removing said sample injection means from said filter means.

9. The method of claim 1 or 2, wherein said step of permitting said vaporizable material to permeate said filter means includes subjecting said sample to a vacuum.

10. The method of claim 9, wherein said sample is simultaneously subjected to centrifugation and said vacuum so as to at least partially lyophilize said sample.

11. The method of claim 9, wherein said sample is simultaneously subjected to centrifugation and said vacuum under conditions not permitting lyophilization of said sample.

12. The method of claim 1 or 2, wherein said step of permitting said vaporizable material to permeate said filter means includes providing means exterior said container for reducing the presence of said material outside said container.

13. The method of claim 3, wherein said container is configured to withstand a high speed centrifugation of about 1500 or more times the force of gravity.

14. The method of claim 13, wherein said container is configured to withstand a high speed centrifugation of about 3000 or more times the force of gravity.

15. The method of claim 1 or 2, wherein said step of providing said container containing said sample includes placing a liquid sample in said container.

16. The method of claim 15, further comprising the step of sealing said opening in said container with a cap.

17. The method of claim 1 or 2, wherein said container is a centrifuge bottle.

18. The method of claim 1 or 2, wherein said container is a centrifuge tube.

19. The method of claim 1 or 2, wherein said sample includes at least one of a protein, a nucleic acid, a peptide, a sugar, and a lipid.

20. The method of claim 1 or 2, wherein said sample includes a material subject to decomposition or denaturation when not lyophilized.

21. The method of claim 1 or 2, wherein said filtering means does not permit substantial permeation therethrough of materials having a diameter greater than about 0.2 microns.

22. The method of claim 1 or 2, wherein said container is configured to withstand centrifugation of about 50 or more times the force of gravity.

23. The method of claim 22, wherein said container is configured to withstand a high speed centrifugation of about 1500 or more times the force of gravity.

24. The method of claim 22, wherein said container is configured to withstand a high speed centrifugation of about 3000 or more times the force of gravity.

25. The method of claim 2, wherein said container includes a cylindrical portion and a conical portion.

* * * * *